United States Patent [19]
Ashbrook

[11] Patent Number: 6,066,667
[45] Date of Patent: May 23, 2000

[54] SUBSTITUTED FURANONES, COMPOSITIONS AND ANTIARTHRITIC USE

[76] Inventor: Charles D. Ashbrook, 2700 Winter Garden Ct., Ann Arbor, Mich. 48105

[21] Appl. No.: 09/375,350

[22] Filed: Aug. 17, 1999

[51] Int. Cl.$^7$ .................... A61K 31/365; C07D 307/33
[52] U.S. Cl. .................. 514/471; 549/321; 549/323; 549/324
[58] Field of Search .................. 514/471; 549/321, 549/323, 324

[56] References Cited

U.S. PATENT DOCUMENTS

| | | | |
|---|---|---|---|
| 4,087,544 | 5/1978 | Salinger et al. | 424/305 |
| 5,474,995 | 12/1995 | Ducharme et al. | 514/241 |

*Primary Examiner*—Ba K. Trinh
*Attorney, Agent, or Firm*—Charles W. Ashbrook

[57] ABSTRACT

The invention provides substituted furanone antiarthritic and analgesic pharmaceutical agents defined by Formula I,

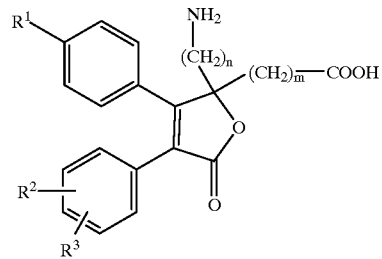

wherein:
R$^1$ is selected from the group consisting of
  (a) S(O)$_2$CH$_3$,
  (b) S(O)$_2$NH$_2$,
  (c) S(O)$_2$NHC(O)CF$_3$,
  (d) S(O)(NH)CH$_3$,
  (e) S(O)(NH)NH$_2$,
  (f) S(O)(NH)NHC(O)CF$_3$,
  (g) P(O)(CH$_3$)OH, and
  (h) P(O)(CH$_3$)NH$_2$;
R$^2$ and R$^3$ independently are selected from
  (1) hydrogen,
  (2) halo,
  (3) C$_1$–C$_6$ alkyl,
  (4) C$_1$–C$_6$ alkoxy, and
  (5) C$_1$–C$_6$ alkylthio;
n is an integer from 1 to 3;
m is an integor from 1 to 3;
or a pharmaceutically acceptable salt thereof.

10 Claims, No Drawings

SUBSTITUTED FURANONES, COMPOSITIONS AND ANTIARTHRITIC USE

FIELD OF THE INVENTION

This invention relates to poly-substituted furanone compounds that are useful for treating pain and arthritis, and to pharmaceutical formulations comprising the compounds and a suitable carrier, and to a method for treating both rheumatoid arthritis and osteoarthritis, and the pain associated with these conditions, by administering a substituted furanone compound.

BACKGROUND OF THE INVENTION

Arthritis is a debilitating disease that afflicts millions of people, and for which there currently are no cures. Several forms of arthritis are known. Rheumatoid arthritis is characterized as a chronic systemic inflammatory disease, primarily of the joints, and generally marked by inflammatory changes in the synovial membranes and articular structures and by atrophy and rarefaction of the bones. Osteoarthritis is a noninflammatory degenerative joint disease occurring most often in older persons. It is characterized by degeneration of the articular cartilage, hypertrophy of bone at the margins, and changes in the synovial membrane. Pain and stiffness accompany it, particularly after prolonged physical activity. Osteoarthritis is also referred to as degenerative arthritis, hypertrophic arthritis, and degenerative joint disease. The exact cause of arthritis is still unknown, and there are no cures. The current treatments are designed to relieve the pain, and to diminish the symptoms that accompany the disease. Most of the known treatments are anti-inflammatory agents such as nonsteroidal anti-inflammatory agents (NSAIDs) and cyclooxygenase (COX) inhibitors. Many of these agents, especially the NSAIDs, cause severe side effects such as gastrointestinal damage, thus limiting their clinical use. Several compounds that inhibit a specific cyclooxygenase enzyme, namely cyclooxygenase-2 (COX-2), have been recently developed and are said to have fewer adverse side effects. Because arthritis is such a debilitating disease, especially for an aging population over 50, the need continues for better and more effective agents that reduce the pain and suffering of arthritis, and have few or no side effects.

There has now been discovered a series of substituted furanones that are potent anti-arthritic agents, and are especially effective for inhibiting the pain that accompanies arthritis. Ducharme et al., in U.S. Pat. No. 5,474,995, disclose several thiophene, isothiazole and furan compounds that can be substituted with groups such as phenyl and alkyl. The compounds are said to be cyclooxygenase inhibitors, and as such, are said to be effective in treating various forms of pain, and inflammatory diseases, including arthritis. The reference fails to describe or suggest furanones having aminoalkyl and carboxy alkyl substituents as now required. An object of this invention is to provide new chemical compounds characterized as being substituted furanones, pharmaceutical formulations containing such furanones, and a method for treating arthritis and pain by administering such furanones.

SUMMARY OF THE INVENTION

This invention provides compounds of Formula I

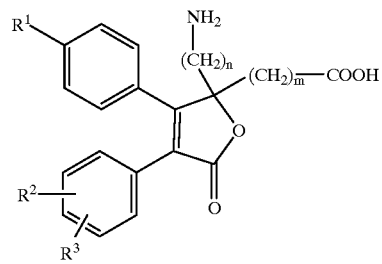

wherein:
R$^1$ is selected from the group consisting of
(a) S(O)$_2$CH$_3$,
(b) S(O)$_2$NH$_2$,
(c) S(O)$_2$NHC(O)CF$_3$,
(d) S(O)(NH)CH$_3$,
(e) S(O)(NH)NH$_2$,
(f) S(O)(NH)NHC(O)CF$_3$,
(g) P(O)(CH$_3$)OH, and
(h) P(O)(CH$_3$)NH$_2$;
R$^2$ and R$^3$ independently are selected from
(1) hydrogen,
(2) halo,
(3) C$_1$–C$_6$ alkyl,
(4) C$_1$–C$_6$ alkoxy, and
(5) C$_1$–C$_6$ alkylthio;
n is an integer from 1 to 3;
m is an integer from 1 to 3;
or a pharmaceutically acceptable salt thereof.

In a preferred embodiment, the invention compounds have Formula II

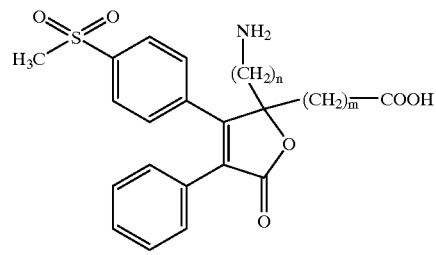

The most preferred compounds are those of Formula II wherein n is 1 or 2, and m is 1 or 2.

Another embodiment of this invention is a pharmaceutical formulation comprising a compound of Formula I together with a pharmaceutically acceptable carrier, excipient, or diluent therefor. A preferred formulation comprises a compound of Formula II together with a carrier, excipient or diluent therefor.

In still a further embodiment of this invention, there is provided a method for treating pain and arthritis comprising administering an effective amount of a compound of Formula I to a mammal suffering from pain or arthritis and in need of treatment.

DETAILED DESCRIPTION OF THE INVENTION

As used herein, the term "C$_1$–C$_6$ alkyl" means straight and branched hydrocarbon chains having from 1 to 6 carbon atoms. Examples include methyl, ethyl, isopropyl, tert-butyl, n-hexyl, and neo-pentyl. "$C_1$–$C_6$ alkoxy" groups are the foregoing alkyl groups bonded at the point of attachment through an oxygen atom. Examples of such alkoxy groups include methoxy, ethoxy, n-propoxy, isobutoxy, n-pentyloxy, and 2,3-dimethylbutoxy. "$C_1$–$C_6$ Alkylthio" means the foregoing alkyl groups bonded at the point of attachment through a sulfur atom. Examples of typical alkylthio groups include methylthio, ethylthio, isopropylthio, n-butylthio, and n-hexylthio.

The terms "n" and "m" in Formula I are integers from 1 to 3. For example, "n" can be 1, 2, or 3, and "m" can be 1, 2, or 3. Preferred compounds have Formula I wherein n is 1 or 2, and m is 1 or 2. Other typical compounds have Formula I wherein n is 1 and m is 2, and those wherein n is 2 and m is 3.

The term "halo" means a halogen atom and includes fluoro, chloro, bromo, and iodo.

The term "pharmaceutically acceptable salt" refers to those carboxylic acid salts and amino acid addition salts formed by reacting a compound of Formula I with an organic or inorganic acid, or an organic or inorganic base. The term "salts" refers to relatively nontoxic salts that can be prepared as final products for use as pharmaceutical agents, or alternatively that are prepared in situ during the last step in the synthesis of an invention compound so as to facilitate isolation and purification. Representative acid addition salts are made by reacting a free amine of Formula I with and organic or inorganic acid, and include salts such as the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, and the like. Typical salts of the carboxylic acids of Formula I are those compounds made by reacting a free carboxylic acid of Formula I with an organic or inorganic base to produce salts such as sodium, lithium, calcium, potassium, magnesium, ammonium, tetramethylammonium, triethylamine, methylamine, benzylamine, and the like. The preparation of these and other typical pharmaceutically acceptable salts is more fully described by Berg et al., "Pharmaceutical Salts," *J. Pharm. Sci.*, 1977:66:1–19.

The substituted furanone compounds of Formula I can be prepared by utilizing any of a number of synthetic processes familiar to those having skill in the art of organic chemistry. One method, for example, comprises a ring closure reaction to form the furanone ring system, as illustrated in Scheme 1. A benzylidene substituted amino alkanoic acid, which is commercially available, or readily prepared by known methods, is protected at the free amino group and at the free carboxy group. In many instances when preparing compounds of Formula I, it may be desirable to protect groups such as hydroxy, amino, and carboxy, with commonly used and easily removable protecting groups. These are groups that can be attached to a hydroxy, amino, or carboxy group for instance, in order to prevent unwanted side reactions at that center during a chemical reaction at another site in the molecule, and then such protecting group is subsequently removed to re-generate the original functional group. A wide variety of protecting groups are known in the art and are routinely utilized in synthetic procedures. Typical groups used to protect hydroxy groups include acyl groups such as formyl and acetyl, as well as groups such as benzyl, trimethylsilyl, and the like. Amino groups are readily protected by reaction with acyl groups such as acetyl, and tert-butoxycarbonyl (BOC), and arylalkyl groups such as p-nitrobenzyl and the like. Carboxy groups are generally protected by conversion to esters such as 2,2,2-trichloroethyl, benzyl, trimethylsilyl, and the like. Examples of these and other protecting groups, and their use in organic synthesis, is fully described by Greene, *Protective Groups in Orgawic Synthesis*, John Wiley & Sons, 1981.

As shown in Scheme I, the free amino group is readily protected by reaction with di-tert-butyl dicarbonate to provide the N-tert-butoxycarbonyl (N-BOC) derivative. The N-BOC protected compound, having a free carboxy group, is then reacted with an ester forming alcohol, such as methanol or ethanol, to provide the corresponding N-protected carboxy-protected benzylidene amino alkanoic acid. The protected intermediate is next reacted with a halogenating agent such as N-bromosuccinimide to produce an alpha halo benzyl substituted hydroxy amino alkanoic acid. This reaction is generally carried out in a solvent such as aqueous dioxane or aqueous dimethylsulfoxide, and typically at a temperature of about 0° C. to about 80° C. The alpha halo benzyl intermediate is then reacted with a phenyl ketone under Wittig conditions (i.e., with triphenylphosphine in tetrahydrofuran) to produce a 4-hydroxy butenoic acid intermediate, which is readily dehydrated by reaction with trifluoroacetic acid, silica or other typical dehydrating agents to effect cyclization to provide the desired substituted furanone. The amino and carboxy protecting groups are removed by conventional methods, such as by reaction with trifluoroacetic acid. The product furanone of Formula I is isolated and purified by routine methods such as crystallization, salt formation, chromatography, and the like.

Another method for preparing the invention compounds is described in Scheme 2. According to this method, a hydroxy substituted alkanoic acid ester is first protected with a suitable protecting group such as trimethylsilyl. The protected hydroxy substituted alkanoic acid is reacted with about an equimolar quantity of a substituted ($R^1$) phenyllithium to provide a protected phenyl ketone derivative. The phenyl ketone is then reacted with one equivalent of tetra n-butylammonium fluoride to remove the hydroxy protecting group. The hydroxy substituted phenyl ketone derivative is next reacted with about an equimolar amount of a substituted or disubstituted ($R^2$ and $R^3$) phenyl acetyl halide (such as chloride or bromide), in the presence of a base such as triethylamine, to provide the corresponding phenylacetoxy substituted phenyl ketone derivative, which is next cyclized by reaction with an agent such as 1,8-diazobicyclo [5.4.0]undec-7-ene (DBU) to give a fully substituted furanone. Any remaining protecting groups can then be removed by conventional methods, such as hydrogenation or by reaction with a base such as tetra n-butylammonium fluoride, to provide the compound of Formula I. The invention compound can be further purified if desired by standard methods including salt formation and crystallization, and chromatography.

Still another method for preparing the invention compounds comprises cleavage of a lactam ring according to Scheme 3 by reaction with a strong acid such as trifluoroacetic acid, or an agent such as mercuric acetate. A hydroxy substituted lactam is first acylated with a substituted or disubstituted phenyl acetyl halide as shown in Scheme 2 to give a phenylacetoxy substituted phenyl ketone. The latter intermediate is cyclized into a furanone by reaction with an agent such as DBU. These reactions are carried out in an unreactive solvent such as acetonitrile or dioxane. The product, a substituted furanone of Formula I, is readily isolated by removal of the reaction solvents, and further purification can be accomplished if desired by standard methods such as chromatography and the like.

Another method for preparing the invention compounds comprises reacting a 3,4-di(substituted phenyl)-2(5H) furanone with one molar equivalent of a strong base such as sodium hydride, under anhydrous conditions (e.g., dry N,N,-dimethylformamide) to produce a carbanion at the furanone 5-position, and then reacting the carbanion with an aminoalkyl halide ($H_2N$ $(CH_2)_n$—X, where X is halo such as chloro or bromo), to produce a furanone having an aminoalkyl substituent at the 5-position. This 5-aminoalkyl furanone is then reacted further with the additional strong base (e.g., one or more equivalents of sodium hydride), and a carboxyalkyl halide ($HOOC(CH_2)$—X), to produce the invention compound of Formula I. These reactions are depicted in Scheme 4 below. The reaction is generally conducted in an unreactive solvent such as toluene, DMF or dioxane, and normally is substantially complete in about 2 to about 8 hours when carried out at about −30° C. to about +30° C. The product can be readily isolated by simply removing the reaction solvent, for instance by evaporation under reduced pressure, and the product can be further purified if desired by routine methods such as salt formation and crystallization, or chromatography over common solid supports such as silica gel and eluting with solvents such as ethyl acetate or methanol.

Another method for preparing the invention compounds comprises reacting an appropriately substituted phenyl bromomethyl ketone with an appropriately substituted phenyl acetic acid, as illustrated in Scheme 5. The reactants are generally combined in approximately equimolar amounts in a mutual solvent such as acetonitrile or dioxane, and stirred in the presence of a base such as triethylamine or pyridine, normally at a temperature of about 0° C. to about 60° C. The reaction mixture is then reacted with a cyclizing agent such as 1,8-diazobicyclo[5.4.0]undec-7-ene (DBU) to afford the invention compound. The product is readily isolated by filtering the reaction mixture, removing the reaction solvent by evaporation, and dissolving the residue in a water immersible solvent such as diethyl ether or ethyl acetate. The organic solution is then washed several times with water, or an aqueous brine solution, and then dried over magnesium sulfate and concentrated to dryness by evaporation of the solvent under reduced pressure.

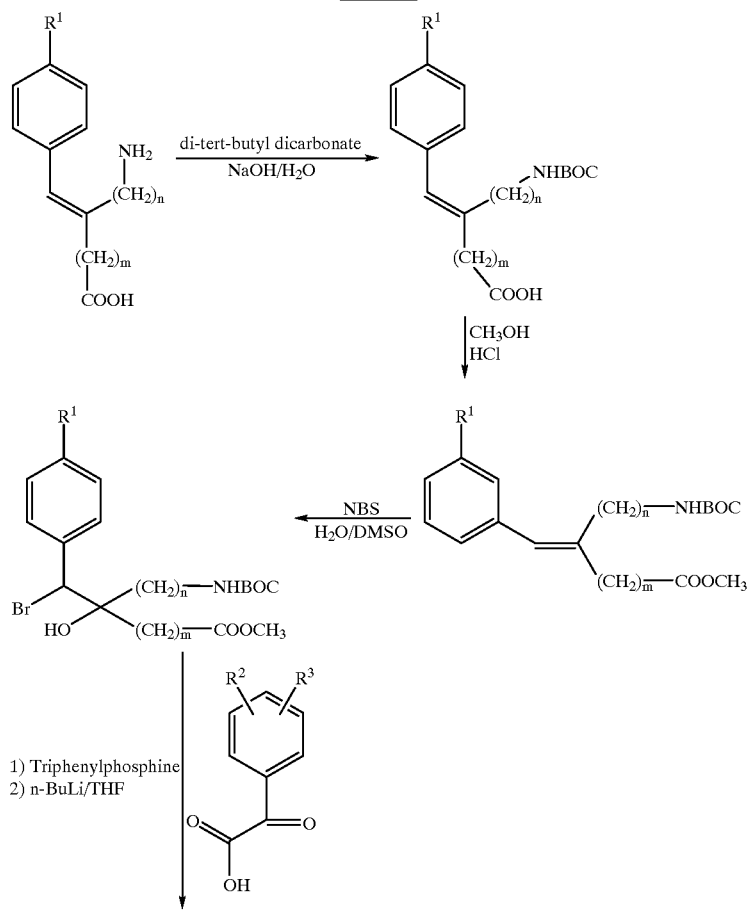

Scheme 1

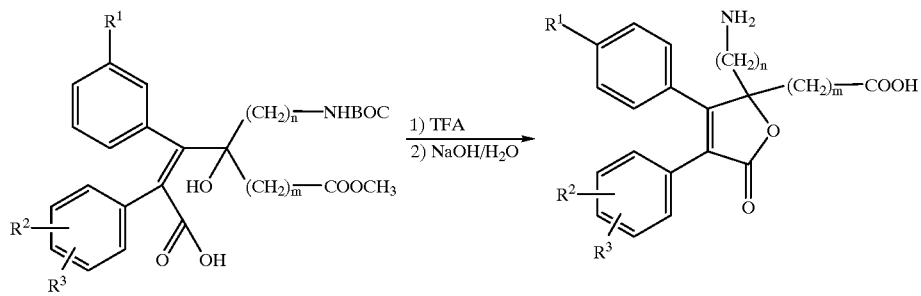
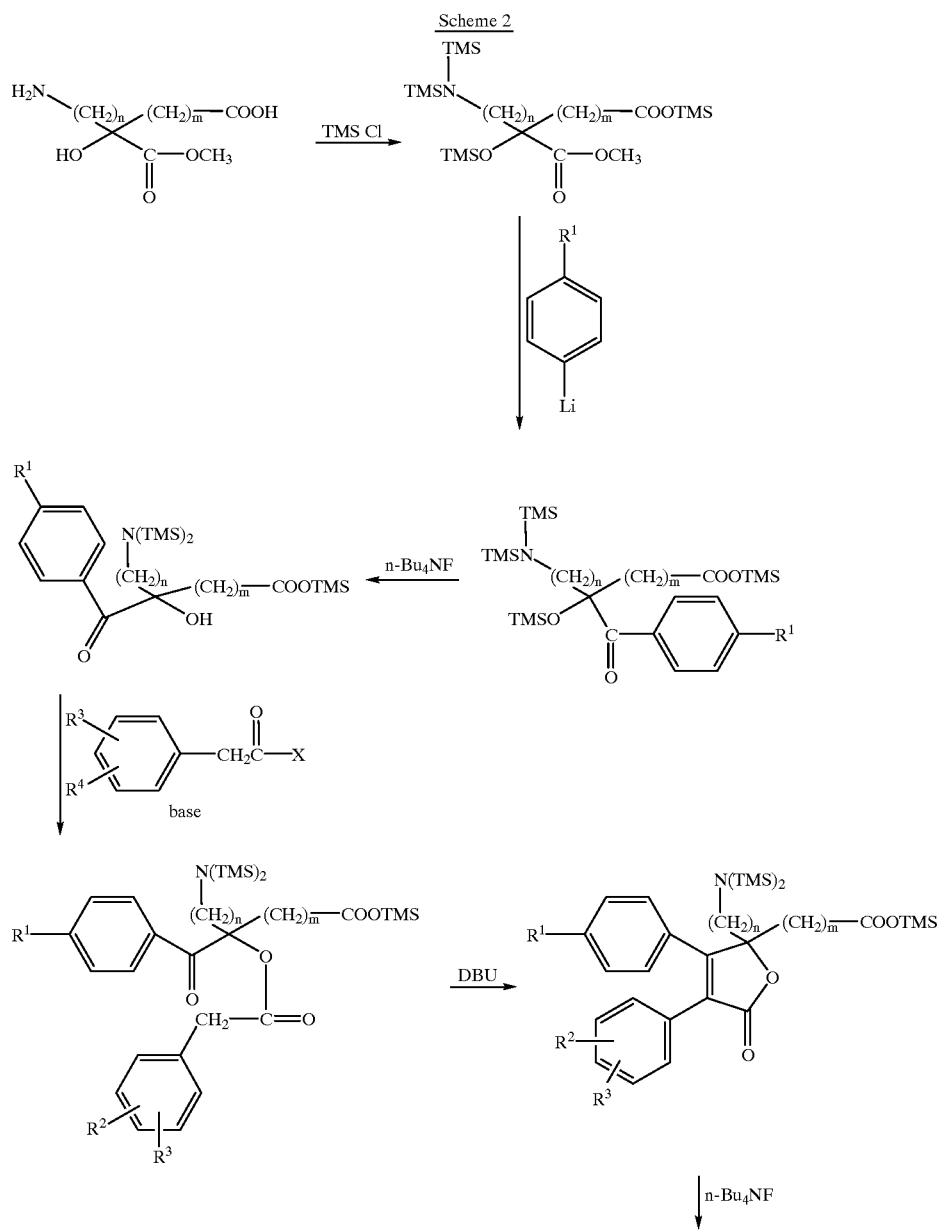

-continued
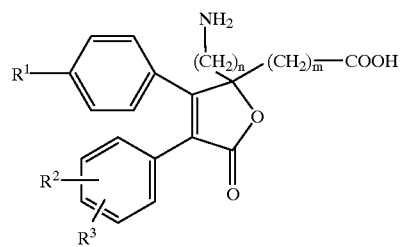
Scheme 3
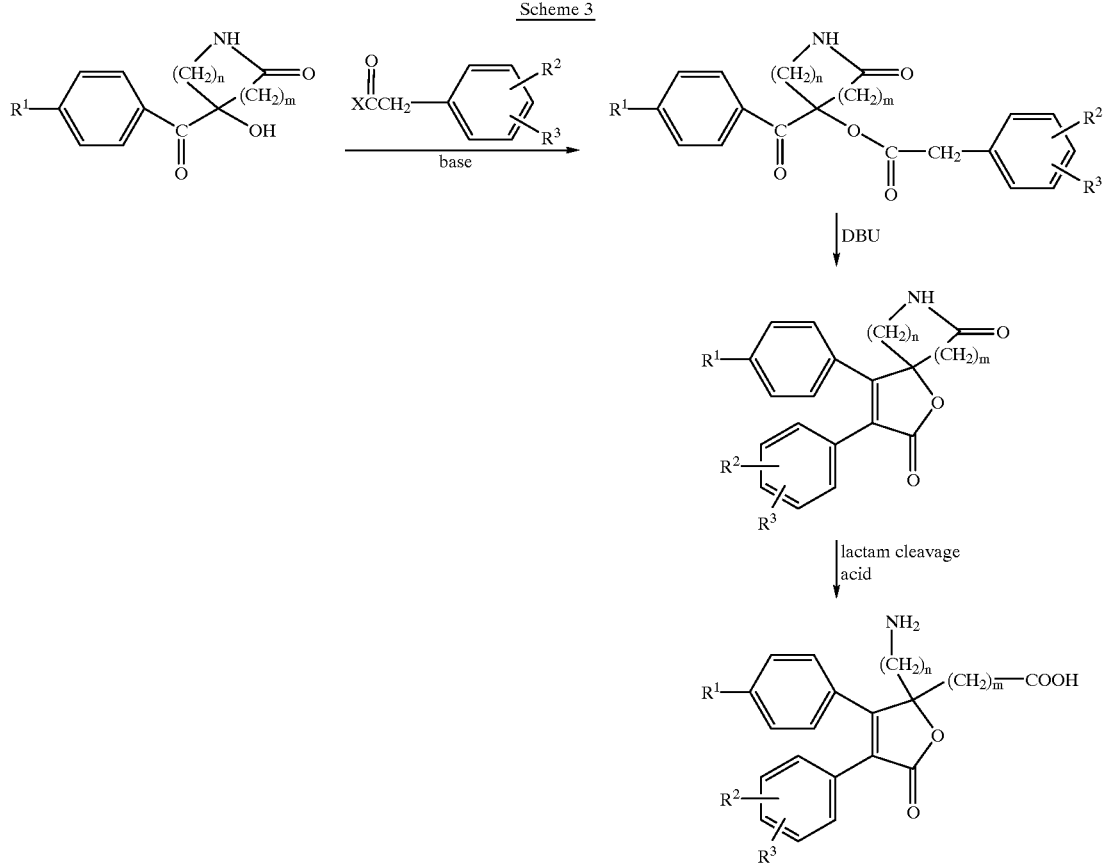
Scheme 4
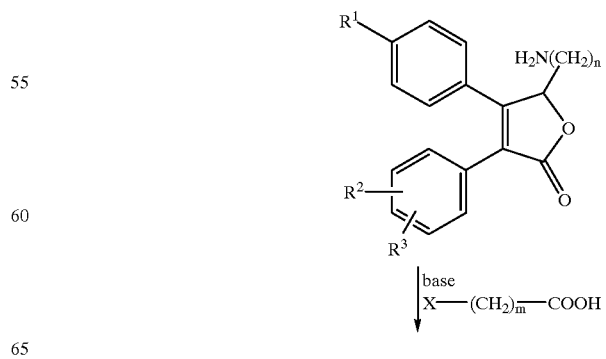

-continued

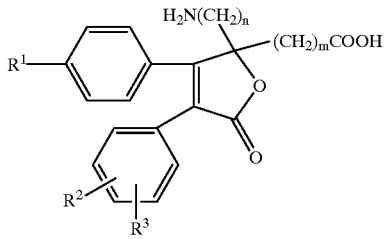

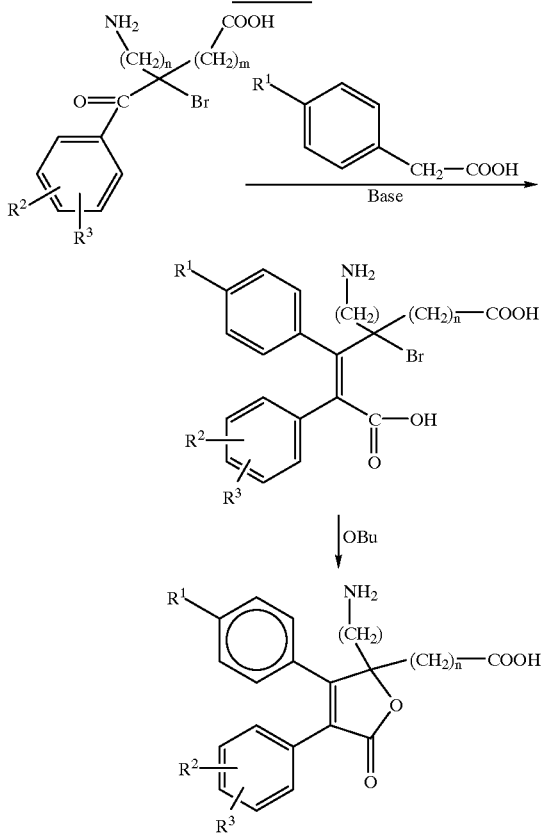

The following examples illustrate specific embodiments of this invention, but are not to be construed as limiting in any respect.

EXAMPLE 1

Utilizing the processes of Scheme 1, there is prepared 4-(4-(methylsuffonyl)phenyl)-3-phenyl-5-aminomethyl-5-carboxymethyl-2-furanone.

EXAMPLE 2

By following the process of Scheme 2 there is prepared 4-(4-(methylsulfonyl)phenyl)-3-(2-methyl-4-chlorophenyl)-5-aminomethyl-5-(2-carboxyethyl)-2-furanone.

EXAMPLE 3

The compound from Example 1 is reacted with 50% aqueous sodium hydroxide at room temperature. The solvent is evaporated under reduced pressure to give a solid which is the corresponding sodium salt of the 5-carboxymethyl furanone.

As noted above, the substituted furanones of Formula I are useful for the prevention and treatment of pain and arthritis. The compounds are evaluated in standard in vitro and in vivo assays which are designed to measure anti-arthritic activity, and are recognized by those skilled in the art to be valid predictors of clinical efficacy. One such assay involved inducing arthritis in mice by injecting type II collagen. The type II-collagen-induced arthritis (CIA) in mice is recognized as an experimental model of arthritis that has a number of pathologic, immunologic, and genetic features in common with rheumatoid arthritis in humans. The disease is induced by immunization of DBA/1 inbred strain of mice with 100 micrograms of type II collagen (C II), which is the major component of joint cartilage. The collagen was delivered to the mice by intradermal injection of a solution made up in Freund's complete adjuvant. A progressive and inflammatory arthritis develops in the majority of the mice immunized, characterized by paw width increases of up to 100%. A clinical scoring index is used to assess disease progression from erythema and edema (stage 1), joint distortion (stage 2), to joint ankylosis (stage 3). The disease is variable in that it can affect one or all of the paws of the animal, resulting in total possible score of 12 for each mouse. Histopathology of arthritic joints revealed synovitis, pannus formation, and cartilage and bone erosions. All mouse strains that are susceptible to CIA are high antibody responders to type II collagen, and there is a marked cellular response to C II.

In another standard assay, monoarticular arthritis was induced in rats. Rats were given 6 microgram doses of sonicated Streptococcal cell wall (SCW) [in 10 microliters of Dulbecco's phosphate buffered saline (DPBS)] by intra-articular injection into the right tibiotalar joint on Day 0. SCW induces paw swelling in the animals. On Day 21, the delayed-type hypersensitivity (DTH) was initiated with 100 micrograms of SCW administered intravenously. Test compounds were suspended in an aqueous mixture of 0.5% HPMC and 0.2% Tween 80, sonicated, and administered twice daily in equally divided doses (10 mL/kg volume) beginning 1 hour prior to reactivation with SCW. The amount of edema was determined by measuring the baseline volumes of the sensitized hindpaw before reactivation on Day 21, and comparing them with the volumes at subsequent time points. Paw volumes were measured by mercury plethysmography.

The invention compounds can also be evaluated in the following assay.

New England White rabbits were euthanized with B-euthanasia administered IV with a 25 gauge needle in the marginal ear vein. The synovium was immediately removed by the incision of the quadracep tendon and retracting the petclia. The synovium, with the infrapellar fat body, was then cut away from the patellar ligament and placed in sterile phosphate buffered saline (PBS) (Gibco BRL, Gaithersberg, Md.). The synovium was finely minced with a sterile scalpel and placed in a 50 mL tube containing 6 mL of a solution of 4 mg collagenase type I (Gibco BRL, Gaithersberg, Md.)/mL PBS. The mixture was incubated for 3 hours at 37° C. During the incubation, the 50 mL tube was gently swirled 4 to 6 times. The synoviocytes were then washed twice in media (the media composition is described below). Washed cells were seeded into one T-75 plastic cell culture flask and incubated at 37° C. in 5% $CO_2$. After reaching 90–100% confluency, the cells were seeded into appropriate containers for the assay. Synovial fibroblasts were allowed to grow for three days after reaching confluency in 96 well plates before testing. Vehicle (0.1% dimethylsulfoxide in media), or a substituted furanone test compound dissolved in vehicle, was added to the synovial fibroblasts 30 minutes before addition of IL-1α. Interleukin-1α (100 U/mL) (Genzyme, Cambridge, Mass.) was suspended in media and added in a volume of 10 μ/well. The cells were then incubated for 24 hours before the media was removed and stored at −20° C. Prostromelysin-1 levels were measured using an ELISA from Amersham (Cat. No. RPN2615). Percent inhibition was determined by comparing the stromelysin-1 concentration of drug-treated cells to that of vehicle-treated controls. The drug concentration at which 50% inhibition of stromelysin-1 production was measured ($IC_{50}$) was determined using linear regression analysis.

The media used in the foregoing assay was prepared as follows, utilizing commercial reagents acquired from Gibco BRL (Gaithersberg, Md.) unless otherwise stated. To each 500 mL bottle of alpha-modified Eagles medium (α-MEM, Cat. No. 12561-023) was added 10 mL of 1 Molar N-2-hydroxyethylpiperazine-N-2-ethane sulfonic acid (1 M HEPES, Cat. No. 15630-023), 10 mL of Penicillin/Streptomycin Stock (Cat. No. 15070-030, 5,000 U/mL Pen./5,000 μg/mL Strep), 500 μL Gentamicin Stock (50 mg/mL) (Cat. No. 15750-011), 40 mL Fetal Calf Serum from Hyclone Inc. (Cat. No. A1111-L).

In a further embodiment of this invention, the compounds can be formulated into compositions suitable for administering to animals, including humans, for treating and preventing arthritis and associated pain. The compounds can be formulated for administration by any route, for instance orally, parenterally, topically, and rectally. For oral administration, for example, an invention compound can be mixed with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5% to about 80% of the weight of the unit. The amount of active compound in such therapeutically useful compositions is such that a therapeutically effective dosage will be obtained. Preferred compositions or preparations according to the present invention are prepared so that an oral dosage unit form contains between about 5 and 1000 mg of active compound, and ideally about 25 to about 750 mg.

The tablets, troches, pills, capsules, and the like may also contain common pharmaceutical excipients such as binders, sweeteners, and the like. Typical binders include gum tragacanth, acacia, corn starch, and gelatin, as well as excipients such as dicalcium phosphate. Typical disintegrating agents include corn starch, potato starch, alginic acid, and the like. A commonly used lubricant is magnesium stearate. Typical sweetening agents are sucrose, lactose, or saccharin, and flavoring agents such as peppermint, oil of wintergreen, or cherry flavoring can be utilized. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially nontoxic in the amounts employed.

The substituted furanone compounds of the invention can also be formulated for topical administration, for instance as patches, salves, creams, ointments, and the like. Agents commonly utilized to enhance transdermal passage can also be employed. The compounds can also be formulated with waxes and the like for convenient rectal administration.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 25 to about 750 mg being preferred. Expressed in proportions, the active compound is generally present in from about 10 to about 750 mg/mL of carrier. In the case of compositions containing supplementary active ingredients, the dosages are determined by reference to the usual dose and manner of administration of the said ingredients. The unit dosages typically will be administered from one to four times per day, or as otherwise needed to effect treatment of the disease state.

The following examples further illustrate the formulations of this invention.

EXAMPLE 4

Soft gelatin capsules are prepared using the following ingredients:

|  | Quantity (mg/capsule) |
| --- | --- |
| Compound of Example 1 | 250.0 |
| Butylated hydroxyanisole B.P. | 0.05 |
| Fractionated Coconut Oil B.P. | 70.0 |
|  | 320.05 |

The above ingredients were mixed and filled into a soft gelatin capsule, the shell components of which were gelatin and glycerine. The capsules are administered at the rate of one to four times a day.

EXAMPLE 5

Tablets are prepared using the following components:

| Compound of Example 2 | 500 mg |
| --- | --- |
| Microcrystalline Cellulose | 200 mg |
| Sodium Carboxymethyl Starch | 20 mg |
| Magnesium Stearate | 4 mg |
| Butylated Hydroxyanisole B.P. | 0.002 mg |

The ingredients were blended to uniformity and compressed into a tablet for oral administration. One to four tablets are administered daily for treatment of arthritis and pain.

EXAMPLE 6

An aerosol is prepared as follows:

| Compound of Example 1 | 100 mg |
| --- | --- |
| Propylene glycol | 20 mg |
| Dichlorotetrafluoroethane (Propellant 14) | 600 mg |
| Dichlorodifluoromethane (Propellant 12) | 500 mg |

The components are mixed at −20° C. and placed into a sealed can equipped with a metering device.

EXAMPLE 7

A solution is prepared as follows:

| Compound of Example 2 | 5 mg |
| --- | --- |
| Water | 1 L |
| 1N HCl | 20 mL |

The ingredients are mixed to form a solution which can be utilized in order to prevent pain.

A further embodiment of this invention is a method of treating, preventing, and combatting pain and arthritis. The method comprises administering an effective amount of a compound of this invention to a subject in need of treatment. The compounds can be administered to animals, especially humans, to treat and prevent pain and both rheumatoid arthritis and osteoarthritis. As noted above, an effective amount of the active compound is that amount that is effective to prevent or treat the pain or arthritic condition, and generally is about 5 to about 1000 mg per dosage unit, and ideally about 25 to about 750 mg.

The active ingredients of the therapeutic compositions and the compounds of the present invention exhibit excellent antiarthritic activity when administered in amounts ranging from about 1.0 to about 100 mg/kg of body weight per day. A preferred dosage regimen for optimum results would be from about 2.0 to about 50 mg/kg of body weight per day, and such dosage units are employed so that a total of from about 0.2 to about 3.0 g of the active compound for a subject of about 70 kg of body weight are administered in a 24-hour period. This dosage regimen may be adjusted to provide the optimum therapeutic response and is preferably administered one to four times a day in dosages of about 250 to about 750 mg per administration. For example, several divided doses may be administered daily, or the dose may be proportionally reduced as indicated by the exigencies of the therapeutic situation. A decided practical advantage is that the active compound may be administered in a convenient manner such as by the oral, intravenous (where water soluble), intramuscular, or subcutaneous routes.

What is claimed is:

1. A compound of Formula I

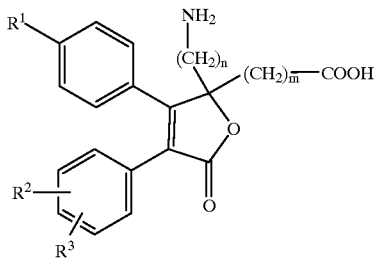

wherein:
$R^1$ is selected from the group consisting of
- (a) $S(O)_2CH_3$,
- (b) $S(O)_2NH_2$,
- (c) $S(O)_2NHC(O)CF_3$,
- (d) $S(O)(NH)CH_3$,
- (e) $S(O)(NH)NH_2$,
- (f) $S(O)(NH)NHC(O)CF_3$,
- (g) $P(O)(CH_3)OH$, and
- (h) $P(O)(CH_3)NH_2$;

$R^2$ and $R^3$ independently are selected from
- (1) hydrogen,
- (2) halo,
- (3) $C_1$–$C_6$ alkyl,
- (4) $C_1$–$C_6$ alkoxy, and
- (5) $C_1$–$C_6$ alkylthio;

n is an integer from 1 to 3;
m is an integer from 1 to 3;
or a pharmaceutically acceptable salt thereof.

2. A compound of claim 1 wherein $R^1$ is $SO_2CH_3$.

3. A compound of claim 2 wherein $R^2$ and $R^3$ both are hydrogen.

4. A compound of claim 3 having Formula II

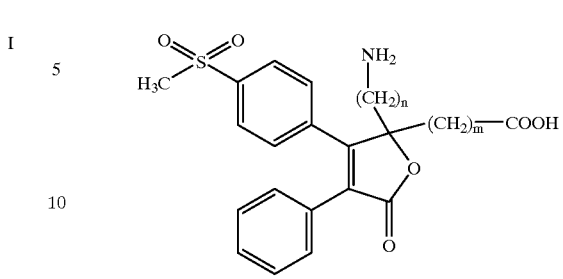

5. A compound which is 4-(4-(methylsulfonyl)phenyl)-3-phenyl-5-aminomethyl-5-carboxymethyl-2-furanone.

6. A pharmaceutical formulation comprising a compound of claim 1 admixed with a pharmaceutically acceptable carrier, excipient, or diluent therefor.

7. A pharmaceutical formulation comprising 4-(4-(methylsulfonyl)phenyl)-3-phenyl-5-aminomethyl-5-carboxymethyl-2-furanone and a pharmaceutically acceptable carrier, diluent, or excipient therefor.

8. A method of preventing or treating pain comprising administering to an animal an effective amount of a compound of claim 1.

9. A method of treating arthritis comprising administering to an animal in need of treatment an effective amount of a compound of claim 1.

10. A method of treating arthritis according to claim 9 wherein the compound administered is 4-(4-(methylsulfonyl)phenyl)-3-phenyl-5-aminomethyl-5-carboxymethyl-2-furanone.

* * * * *